United States Patent [19]

Anderskewitz et al.

[11] Patent Number: 5,731,332
[45] Date of Patent: Mar. 24, 1998

[54] SUBSTITUTED BENZAMIDINE COMPOUNDS WHICH HAVE USEFUL PHARMACEUTICAL ACTIVITY

[75] Inventors: Ralf Anderskewitz, Bingen; Kurt Schromm, Ingelheim; Ernst-Otto Renth, Ingelheim; Franz Birke, Ingelheim; Armin Fügner, Gau-Algesheim; Hubert Heuer, Schwabenheim; Christopher Meade, Bingen, all of Germany

[73] Assignee: Boehringer Ingelheim KG, Ingelheim am Rhein, Germany

[21] Appl. No.: 765,692

[22] PCT Filed: Jun. 3, 1995

[86] PCT No.: PCT/EP95/02112

§ 371 Date: Mar. 28, 1996

§ 102(e) Date: Mar. 28, 1996

[87] PCT Pub. No.: WO96/02497

PCT Pub. Date: Feb. 1, 1996

[30] Foreign Application Priority Data

Jul. 13, 1994 [DE] Germany .......... 44 24 713.3

[51] Int. Cl.⁶ ............ C07D 213/81; C07C 257/18; A61K 31/165; A61K 31/44
[52] U.S. Cl. ............ 514/354; 514/637; 546/328; 564/244; 564/246
[58] Field of Search ............ 546/328; 564/244, 564/246; 514/354, 637

[56] References Cited

FOREIGN PATENT DOCUMENTS 0 518 818  12/1992  European Pat. Off. .
0 518 819  12/1992  European Pat. Off. .
0 601 977   6/1994  European Pat. Off. .
WO 93/16036  8/1993  WIPO .
WO 94/11341  5/1994  WIPO .

*Primary Examiner*—Zinna Northington Davis
*Attorney, Agent, or Firm*—Robert P. Raymond; Alan R. Stempel; Mary Ellen Devlin

[57] ABSTRACT

Compounds of formula

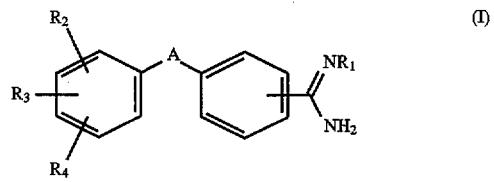

(I)

and their therapeutic use, inter alia, as $LTB_4$-antagonists. Exemplary compounds are:

(Methoxycarbonyl-imino-{4'-[2-(2-propylphenoxy)-ethoxy]-biphenyl-4-yl}-methyl)-amine;

(Benzyloxycarbonyl-imino-{4'-[2-(2-propylphenoxy)-ethoxy]-biphenyl-4-yl}-methyl-amine;

[Hydroxy-imino-(4-{3-[4-(1-methyl-1-phenylethyl)-phenoxymethyl]-benzoyloxy}phenyl)-methyl]-amine;

[Ethoxycarbonyl-imino-(4-{3-[4-(1-methyl-1-phenylethyl)-phenoxymethyl]-benzoyloxy}phenyl)-methyl]-amine; and,

[3'-Pyridylcarbonyl-imino-(4-{3-[4-(1-methyl-1-phenylethyl)-phenoxymethyl]-benzyloxy}phenyl)-methyl]-amine.

14 Claims, No Drawings

SUBSTITUTED BENZAMIDINE COMPOUNDS WHICH HAVE USEFUL PHARMACEUTICAL ACTIVITY

CROSS-REFERENCES TO RELATED APPLICATIONS

This application was field pursuant to 35 U.S.C. §371 and corresponds to International Application Number PCT/EP95/02112, filed on Jun. 3, 1995.

FIELD OF THE INVENTION

The invention relates to new substituted benzamidines, the preparation thereof using conventional methods and their use, as pharmaceuticals with in particular, an $LTB_4$-receptor-antagonist activity.

DESCRIPTION OF THE INVENTION

The new substituted benzamidines correspond to the formula

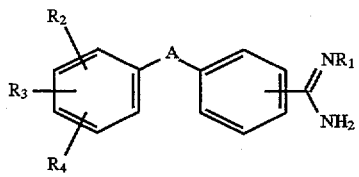
(I)

wherein the
A denotes the group

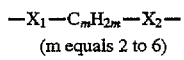
(II)

(m equals 2 to 6)

or

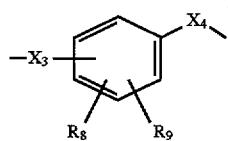
(III)

$X_1$ denotes O, NH or $NCH_3$
$X_2$ denotes O, NH, $NCH_3$ or

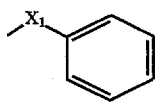
(IV)

$X_3$ denotes —X—$C_nH_{2n}$—;
$X_4$ denotes —$C_nH_{2n}$—X— (n=1 or 2, X=O, NH or $NCH_3$);
$R_1$ denotes OH, CN, $COR_{12}$, $COOR_{12}$ or CHO;
$R_2$ denotes Br, Cl, F, $CF_3$, OH, $C_1$–$C_6$-alkyl, $C_5$–$C_7$-cycloalkyl, aryl, O-aryl, $CH_2$-aryl, $CR_5R_6$-aryl, $C(CH_3)_2$-$R_7$; and also H, when A is a group of Formula III or when $X_2$ is a group of Formula IV; and also $C_1$–$C_6$-alkoxy, when A is the group II, $X_1$ is as hereinbefore defined and $X_2$ denotes NH, $NCH_3$ or the group IV, or when A denotes the group III, $X_3$ is as hereinbefore defined and in $X_4$ X denotes NH or $NCH_3$;
$R_3$ denotes H, $C_1$–$C_6$-alkyl, OH, Cl, F, and also $C_1$–$C_6$ alkoxy when $R_2$ denotes aryl, O-aryl, $CH_2$-aryl, $CR_5R_6$-aryl or $C(CH_3)_2$-$R_7$ or when $X_2$ denotes the group IV;
$R_2$ and $R_3$ may also together denote a fused aromatic or heteroaromatic ring;

$R_4$ denotes H or $C_1$–$C_6$-alkyl;
$R_5$ denotes $C_1$–$C_4$-alkyl, $CF_3$, $CH_2OH$, COOH or COO($C_1$–$C_4$-alkyl);
$R_6$ denotes H, $C_1$–$C_4$-alkyl, or $CF_3$;
$R_5$ and $R_6$ together may also form a $C_4$–$C_6$-alkylene group;
$R_7$ denotes $CH_2OH$, COOH, COO($C_1$–$C_4$-alkyl), $CONR_{10}R_{11}$ or $CH_2NR_{10}R_{11}$;
$R_8$, $R_9$ denote H, Br, Cl, F, OH, $C_1$–$C_6$-alkyl or $C_1$–$C_6$-alkoxy;
$R_{10}$ denotes H, $C_1$–$C_6$-alkyl, phenyl, phenyl-($C_1$–$C_6$-alkyl), $COR_{12}$, $COOR_{12}$, CHO, $CONH_2$, $CONHR_{12}$, $SO_2$-($C_1$–$C_6$-alkyl), $SO_2$-phenyl, wherein the phenyl group may be mono- or polysubstituted by Cl, F, $CF_3$, $C_1$–$C_4$ alkyl, OH, $C_1$–$C_4$-alkoxy;
$R_{11}$ denotes H or $C_1$–$C_6$-alkyl;
$R_{10}$ and $R_{11}$ together may also denote a $C_4$–$C_6$-alkylene group;
$R_{12}$ denotes $C_1$–$C_6$-alkyl, $C_5$–$C_7$-cycloalkyl, aryl, heteroaryl, aralkyl or heteroaryl-($C_1$–$C_6$-alkyl), wherein the aryl or heteroaryl group may be mono or polysubstituted by Cl, F, $CF_3$, $C_1$–$C_4$-alkyl, OH or $C_1$–$C_4$-alkoxy.

The new compounds may occur as free bases or as salts with acids, preferably physiological acceptable acids; if they contain one or more chiral centres, they may be in the form of racemates, in enantiomerically pure or concentrated form, optionally as pairs of diastereomers. Any tautomers (with —C(NH)—$NHR_1$) are also included.

The preferred compounds of Formula I are those wherein A, m, n, $X_3$, $X_4$ and $R_1$ are as hereinbefore defined;
$X_1$ denotes O;
$X_2$ denotes O or a group IV (wherein $X_1$ equals O);
$R_2$ denotes Cl, F, $CF_3$, OH, $C_1$–$C_6$-alkyl, aryl, O-aryl, $CH_2$-aryl or $CR_5R_6$-aryl, and, if $X_2$ is the group IV, $R_2$ may also represent $C_1$–$C_6$-alkoxy;
$R_3$ denotes H, $C_1$–$C_6$-alkyl or OH, and, if $R_2$ $CR_5R_6$-aryl, $R_3$ also denotes $C_1$–$C_6$-alkoxy;
$R_4$ denotes H;
$R_5$ denotes $C_1$–$C_3$-alkyl, $CF_3$ or $CH_2OH$;
$R_6$ denotes H, $C_1$–$C_3$-alkyl or $CF_3$,
$R_5$ and $R_6$ together may also denote $C_4$–$C_5$-alkylene;
$R_8$ and $R_9$ denote H, F or OH.

Particular mention should be made of the compounds wherein, within the scope of the above definitions
$X_1$ denotes O;
$X_2$ represents the group IV (wherein $X_1$ equals O);
X denotes O;
$R_1$ denotes $COOR_{12}$;
$R_2$ denotes $C_1$–$C_6$-alkyl, aryl, O-aryl, $CH_2$-aryl or $CR_5R_6$-aryl;
$R_3$ denotes H, OH or $C_1$–$C_6$-alkyl and, if $R_2$ is $CR_5R_6$-aryl, $R_3$ may also denote $C_1$–$C_6$ alkoxy;
$R_4$ denotes H;
$R_5$ and $R_6$ denote $C_1$–$C_3$-alkyl or $CF_3$;
$R_8$ and $R_9$ denote H;
$R_{12}$ denotes $C_1$–$C_6$-alkyl, aralkyl or $C_7$–$C_5$-cycloalkyl.

Where the symbols according to the above definitions may have the same or different meanings, both possibilities should be included. Aliphatic chains which have a sufficient number of carbon atoms may be straight chained or branched.

"Aryl" denotes an optionally (mono- or poly-) substituted aryl group, such as naphthyl, but preferably an optionally (mono- or poly-) substituted phenyl group. The preferred substituents are: Cl, F, Br, OH, $C_1$–$C_6$-alkyl, $C_1$–$C_6$-alkoxy, and $CF_3$; other possibilities are groups which are generally present only once, such as $NH_2$, $NH(C_1$–$C_6$-alkyl), $N(C_1$–$C_6$-alkyl)$_2$, $NH(SO_2$–$(C_1$–$C_6$-alkyl), $NH(SO_2$-phenyl), wherein the phenyl group may in turn be substituted, in particular by F, Cl, $CF_3$, $C_1$–$C_4$-alkyl, $C_1$–$C_4$ alkoxy or OH. The term "aralkyl" denotes a $C_1$–$C_6$-alkyl group which is substituted by an aryl (as hereinbefore defined). The term "heteroaryl" here preferably refers to pyridyl, pyrimidyl, pyridazinyl and pyrazinyl, thienyl and furyl, which may be mono or polysubstituted, in particular, by Cl, F, Br, OH, $C_1$–$C_6$-alkyl, $C_1$–$C_6$-alkoxy, $CF_3$. The cycloalkyl groups may be substituted by $C_1$–$C_6$-alkyl groups, e.g. as in the menthyl group. If $R_2$ and $R_3$ together denote a fused ring, this refers to a ring which forms a basis for aryl and heteroaryl groups as hereinbefore defined.

In the alkyl and alkoxy groups the number of carbon atoms is preferably between 1 and 4. The preferred substituents in aromatic or heteroaromatic groups are alkyl and alkoxy groups having up to 3, preferably up to 2, carbon atoms. The amidino group $C(NH_2)NR_1$ is preferably in the the para-position relative to Group A.

The new compounds may be obtained by methods known per se, for example as follows:

1. Reacting an amidine as formula

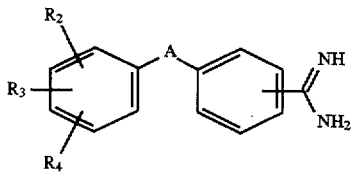

(V)

with a compound of formula

(VI)

wherein in compound (V) A, $R_2$, $R_3$ and $R_4$ are as hereinbefore defined, $R'_1$ has the same meaning as $R_1$, with the exception of OH, and L denotes a nucleophilically exchangeable group such as a halogen atom (such as Cl, Br) or acyloxy. The reaction is appropriately carried out in a solvent such as tetrahydrofuran, methylene chloride, chloroform or dimethylformamide, preferably in the presence of a base such as sodium carbonate, potassium carbonate or sodium hydroxide solution or in the presence of a tertiary organic base such as triethylamine, N-ethyl-diisopropylamine, N-methyl-morpholine or pyridine which may simultaneously serve as solvents, at temperatures between –30° and 100° C., but preferably at temperatures between –10° and 80° C.

2. Reacting compounds of Formula

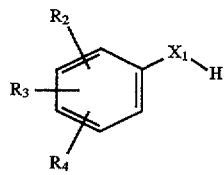

(VII)

(wherein $R_2$, $R_3$, $R_4$ and $X_1$ are as hereinbefore defined), with a benzamidine derivative of Formula

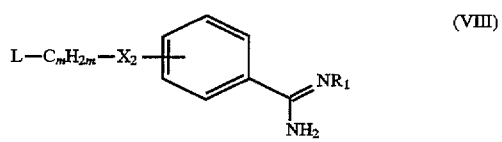

(VIII)

or

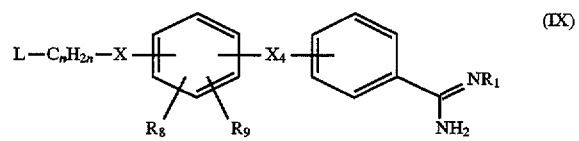

(IX)

(wherein L, m, n, X, $X_2$, $X_4$, $R_1$, $R_8$ and $R_9$ are as hereinbefore defined).

3. Reacting compounds of Formula

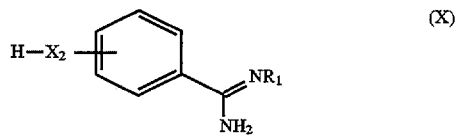

(X)

(wherein $R_1$ and $X_2$ are as hereinbefore defined) with a compound of Formula

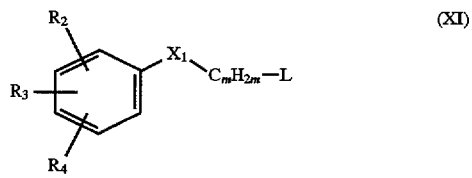

(XI)

or

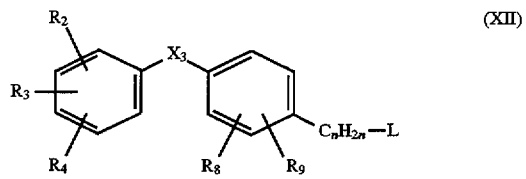

(XII)

(wherein L, m, n, $R_2$, $R_3$, $R_4$, $R_8$, $R_9$, $X_1$ and $X_3$ are as hereinbefore defined). Methods 2 and 3 are preferably carried out in aprotic solvents such as dimethylsulfoxde, dimethylformamide, acetonitrile or alcohols (e.g. methanol, ethanol, isopropanol) with the addition of basic substances (e.g. metal carbonates, metal hydroxides, metal hydrides) at temperatures between about 0° and 140° C. or at the boiling temperature of the reaction mixture.

4. In order to prepare compounds of Formula I wherein $R_1$ denotes OH; a nitrile of formula

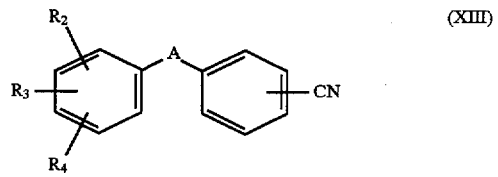

(XIII)

wherein A, $R_2$, $R_3$ and $R_4$ are as hereinbefore defined, as reacted with hydroxylamine. Method 4 is preferably carried out in an alcohol (methanol, ethanol, propanol) or an aprotic solvent such as dimethylsulfoxide, dimethylformamide, or acetonitrile, or optionally in admixture with water, in warm conditions. The hydroxylamine is used, for example, in the form of the hydrochloride or methane sulfonate, and a suitable base such as sodium carbonate is added.

The starting materials may be synthesised using conventional methods.

It has been found that the compounds of Formula 1 are characterised by their versatility in the therapeutic field. Particular mention should be made of those possible applications for which the $LTB_4$-receptor-antagonistic properties come into play. Example include, in particular: arthritis, asthma, chronic obstructive lung diseases, such as chronic bronchitis, psoriasis, ulcerative colitis, gastro or enteropathy induced by non-steroidal antiphlogistics, Alzheimers disease, shock, reperfusion damage/ischaemia, atherosclerosis and multiple sclerosis.

The new compounds may also be used to treat diseases or conditions in which the passage of cells from the blood through the vascular endothelium into tissue is of importance (such as metastasis) or diseases and conditions in which the combination of $LTB_4$ or another molecule (for example 12-HETE) with the $LTB_4$-receptor influences cell proliferation (such as chronic myelocytic leukaemia).

The new compounds may also be used in conjunction with other active substances, e.g. those which are used for the same indications or, for example, with antiallergics, secretolytics, $\beta_2$-adrenergics, steroids administered by inhalation, antihistamines and/or PAF-antagonists. The substances may be administered topically, orally, transdermally, nasally, parenterally or by inhalation.

The new compounds are characterised by being well tolerated and having good bioavailability.

The therapeutic or prophylactic dose depends not only on the potency on the individual compounds and the body weight of the patient, but also on the nature and gravity of the condition. For oral use the dose is between 10 and 500 mg, preferably between 20 and 250 mg. For inhalation a dosage of between 0.5 and 25, preferably between 2 and 20 mg of active substance is delivered to the patient. Inhalation solutions generally contain between about 0.5 and 5% of active substance. The new compounds may be administered, e.g. as plain or coated tablets, capsules, lozenges, powders, granules, solutions, emulsions, syrups, inhalation aerosols, ointments or suppositories.

Pharmacological and biochemical investigation of the activity may be carried out using tests as described for example in WO 16036, Pages 15 to 17.

EXAMPLES OF FORMULATIONS

1. Tablets

Composition:

| Active substance according to the invention | 20 parts by weight |
|---|---|
| Stearic acid | 6 parts by weight |
| Glucose | 474 parts by weight |

The ingredients are processed in the usual way to form tablets weighing 500 mg. If desired, the content of active substance increased or reduced and the quantity of glucose increased or reduced accordingly.

2. Suppositories

Compositions:

| Active substance according to the invention | 100 parts by weight |
|---|---|

-continued

| Powdered lactose | 45 parts by weight |
|---|---|
| Cocoa butter | 1555 parts by weight |

The ingredients are processed in the usual way to form suppositories weighing 1.7 g.

3. Inhalation powder

Micronised powdered active substance (Compound of formula 1; particle size of about 0.5 to 7 μm) is packed into hard gelatine capsules in a quantity of 5 mg, optionally with the addition of micronised lactose. The powder is inhaled from conventional inhalers, e.g. according to DE-A 33 45 722.

The following Examples provide a guide to the preparation of the new compounds.

Example 1
(Methoxycarbonyl-imino-(4'-[2-(2-propylphenoxy)-ethoxy)-biphenyl-4-yl)-methyl)-amine

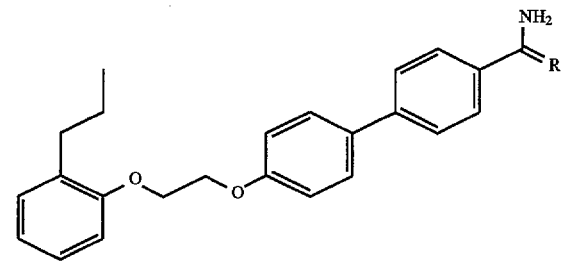

3.8 g of the amidine compound of the above formula (R equals NH), which may be obtained by conventional methods, e.g. using the method according to WO 93/16036, are suspended in 200 ml of chloroform. 1.6 ml of triethylamine are added and 0.8 ml of methyl chloroformate are added dropwise at ambient temperature. After the components have dissolved the mixture is stirred for 3 hours, then extracted three times with water, evaporated down and the residue is stirred with ether and suction filtered. Yield of compound of the above formula wherein R equals $NCOOCH_3$: 3.7 g, melting point 170°–176° C.

Example 2
(Benzyloxycarbonyl-imino-{4'-[2-(2-propylphenoxy)-ethoxy-biphenyl-4-yl}methyl)-amine 2.6 g of the amidine compound of the above formula (R=NH) are placed in 200 ml of chloroform. 1.3 ml of triethylamine are added and 1 ml of benzylchloroformate is added dropwise at ambient temperature. After the components have dissolved, the mixture is stirred for 3 hours, then extracted three times with water, evaporated down and the residue is stirred with ether and suction filtered. The substance is recrystallised from ethanol. Yield of the compound of the above formula wherein R=$NCOOCH_2Ph$: 2.2 g, Mp. 128°–131° C. Compounds with other groups R prepared in an analogous way:
R=$NCOOC_2H_5$; Mp. 120°–123° C.
R=$NCOO$-n-$C_3H_7$; Mp. 113°–114° C.
R=$NCOO$-i-$C_3H_7$; Mp. 110°–117° C.
R=$NCOO$-n-$C_4H_9$; Mp. 135°–138° C.
R=$NCOO$-i-$C_4H_9$; Mp. 103° C.
R=$NCOO$-t-$C_4H_9$; Mp. 129°–132° C.
R=$NCOO$-n-$C_6H_{13}$; Mp. 117°–121° C.

Example 3
3.5 g of the amidine compound of the above formula (R=NH) are placed in 150 ml of chloroform. 2 ml of triethylamine are added and 1 ml of di-tert.-butyldicarbonate is added dropwise at ambient temperature. After the components have dissolved, the mixture is stirred for 3 hours, then extracted three times with water, evaporated down and the residue is stirred with ether and suction filtered. The substance is recrystallised from 20 ml of ethanol. Yield of the compound of the above formula wherein R=N-COO-t-butyl: 3 g, Mp. 129°–132° C.

Example 4
(a) [Hydroxy-imino-(4-{3-[4-(1-methyl-1-phenylethyl)-phenoxymethyl]benzyloxy}phenyl)-methyl]-amine

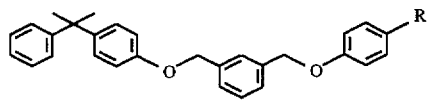

5.25 g of nitrile of the above formula (R=CN, prepared by conventional methods) are placed in 60 ml of ethanol and heated to boiling. In the course of 30 minutes, a solution of 2.7 g of sodium carbonate and 3.4 g of hydroxylamine hydrochloride in 10 ml of water is added dropwise. The mixture is then refluxed for 5 hours. After cooling, the mixture is evaporated down, the residue is taken up in 50 ml of water and extracted three times with 40 ml of ethyl acetate. The organic phases are dried over MgSO$_4$, filtered and concentrated by evaporation. The crystals are taken up in 20 ml of acetone and acidified with ethereal hydrochloric acid. After brief dissolution, 5.3 g of the hydrochloride of the amidoxime of the above formula are obtained wherein R=C(NOH)—NH$_2$. Mp. 180°–181° C.

(b) [Imino-(4-{3-[4-(1-methyl-1-phenylethyl)-phenoxymethyl]-benzyloxy}phenyl)-methyl]-amine

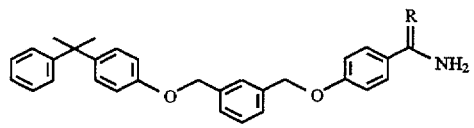

5.1 g of the amidoxime of the above formula (R=NOH) are dissolved in 120 ml of methanol and hydrogenated in the presence of 10 g of methanol-moistened Raney nickel for 2 hours under normal pressure and at ambient temperature. The nickel is removed by suction filtration and the solution is filtered over silica gel. The filtrate is acidified with ethanolic hydrochloric acid, the solution is evaporated down and recrystallised from ethanol. The yield is 3.3 g of the amidine compound (in the above formula, R=NH). Mp. 160° C.

(c) [Ethoxycarbonyl-imino-(4-{3-[4-(1-methyl-1-phenylethyl)-phenoxymethyl]benzyloxy}phenyl)-methyl]-amine 2.44 g of the amidine compound of the above formula (R=NH) obtained according to (b) are placed in 150 ml of dichloromethane, 0.6 g of ethylchloroformate are added, then at ambient temperature 52.5 ml of 0.2N sodium hydroxide solution are added dropwise over 15 minutes. The solution obtained is stirred for 2 hours at ambient temperature, then the organic phase is separated, extracted with 100 ml of water and dried over sodium sulphate. The solution is evaporated down and the residue is recrystallised from 10 ml of ethanol. 2.1 g of title compound are obtained (R=NCOOC$_2$H$_5$), Mp. 99° C.

The following compounds of the formula given in Example 4(b), for example, may be obtained analogously:
R=NCOO-(–)-menthyl; Mp. 113° C.
R=NCO—C$_6$H$_5$; Mp. 101°–103° C.

Example 5
[3'-Pyridylcarbonyl-imino-(4-{3-[4-(1-methyl-1-phenylethyl)-phenoxymethyl]-benzyloxy}phenyl)-methyl]-amine 5.0 g of the amidine compound of the above formula (R=NH, cf. Example 4(b)) are placed in 250 ml of dichloromethane. Over 10 minutes, at ambient temperature, a solution of 3.9 g of nicotinic acid chloride hydrochloride and 16.3 ml of triethylamine in 50 ml of dichloromethane is added dropwise. After 15 hours at ambient temperature the mixture is extracted twice with 300 ml of water, the organic phase is dried over sodium sulphate, filtered and the filtrate is evaporated down. The residue is purified by low-pressure chromatography over silica gel 60 using ethyl acetate, the product is dissolved in 50 ml of acetone, acidified with ethanolic hydrochloric acid and precipitated with ether as its hydrochloride. The yield is 2.0 g of the nicotinoyl derivative of the above formula wherein R=N—CO-3-pyridyl, Mp. 172° C.

The following compounds may also be prepared, inter alia, analogously with the Examples:

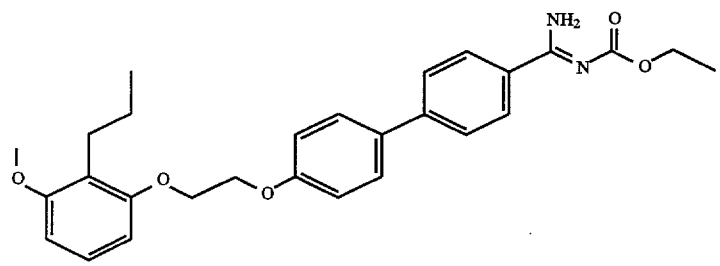

107–111° C

-continued
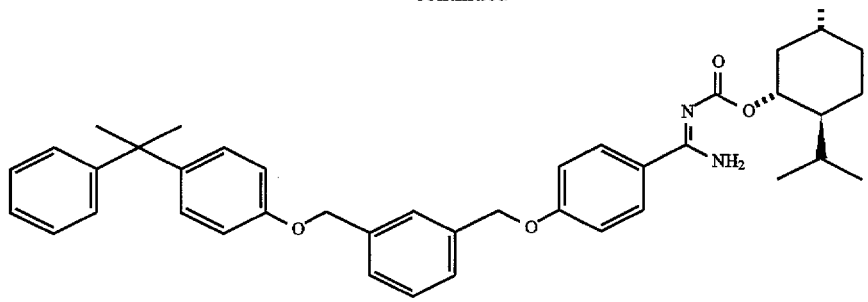
113° C
(−)-Menthylester
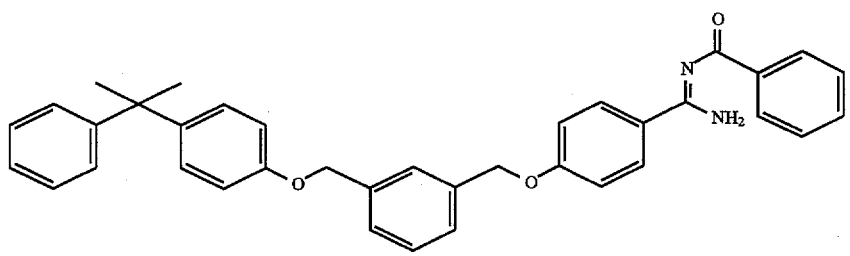
101–103° C
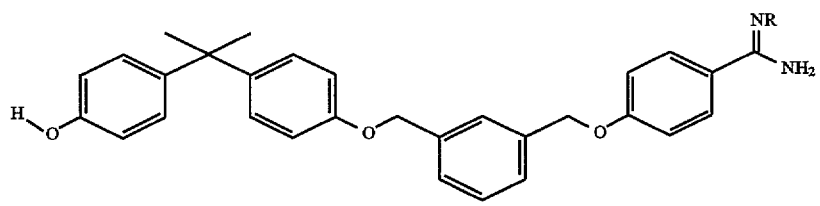
R = OH Mp. 181° C
R = COOC$_2$H$_5$ Mp. 131°C (with 1 mol of ethanol)
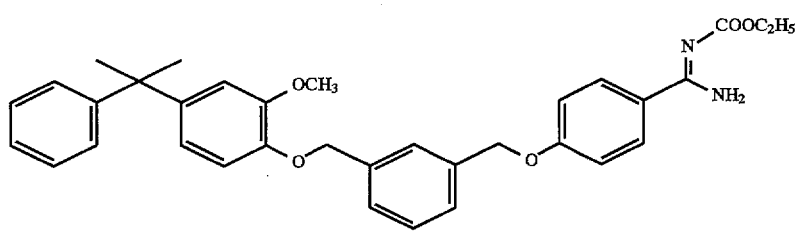
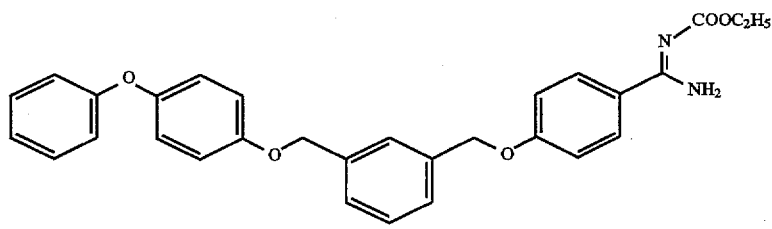
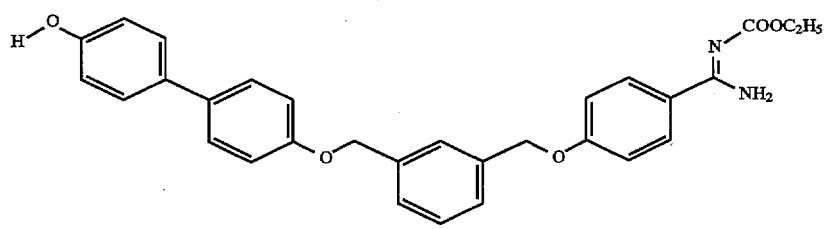

-continued
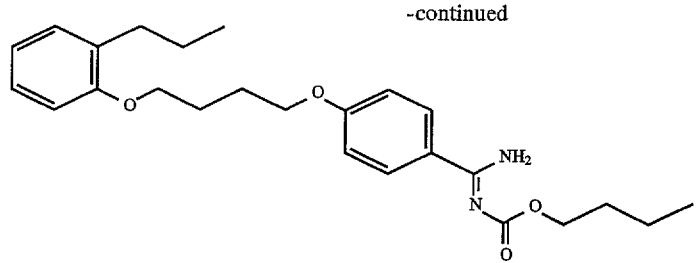
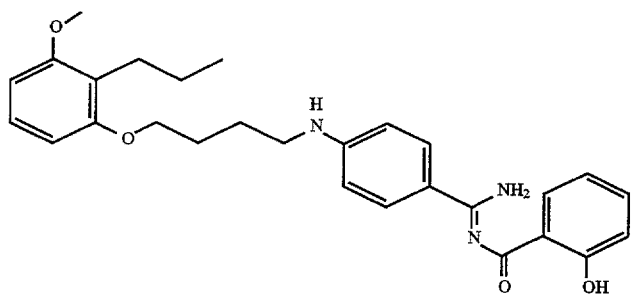
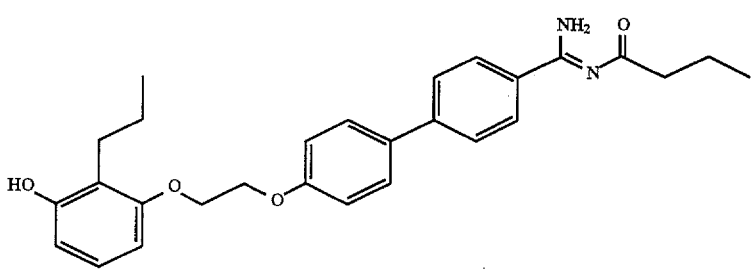
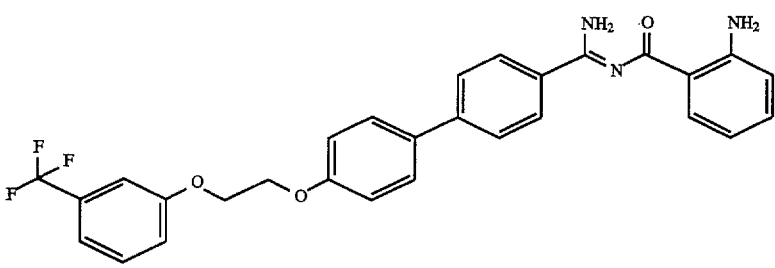
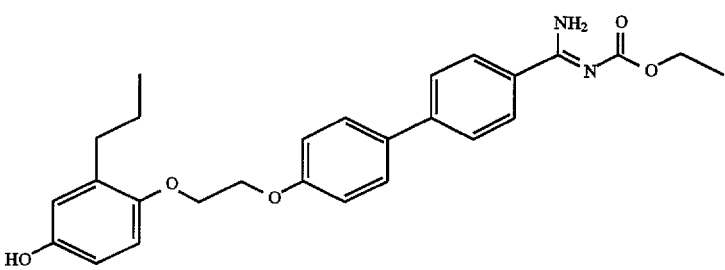
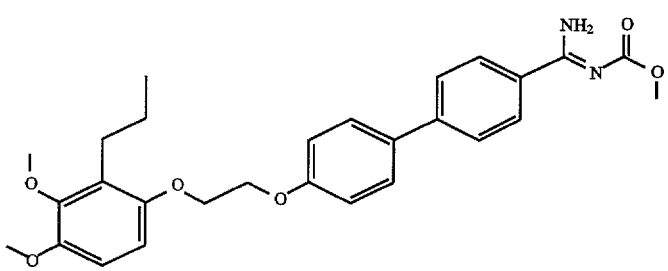

-continued
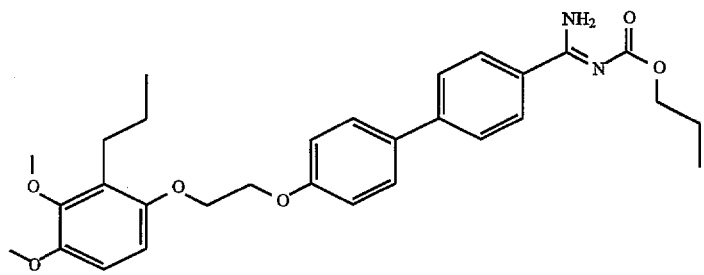
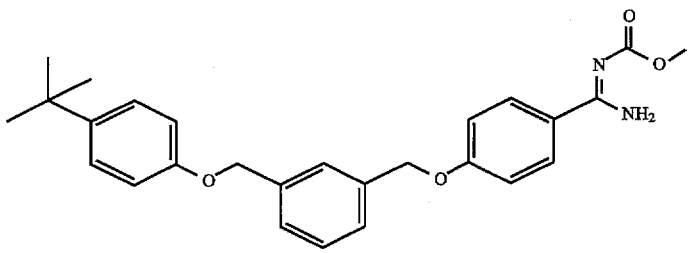
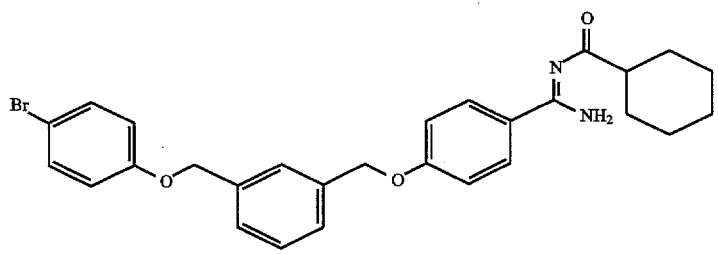
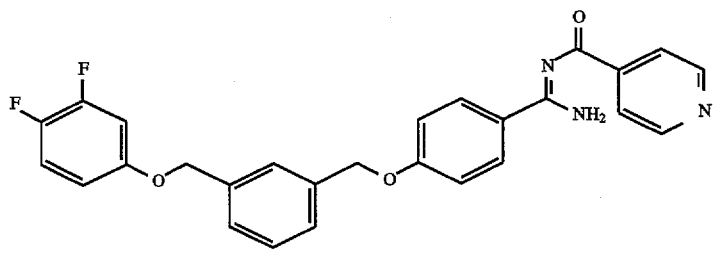
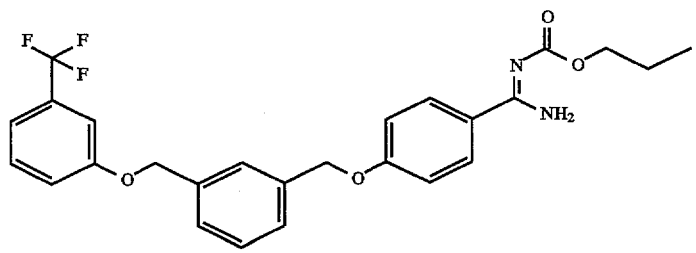
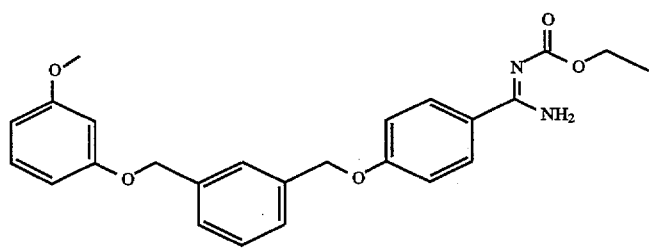

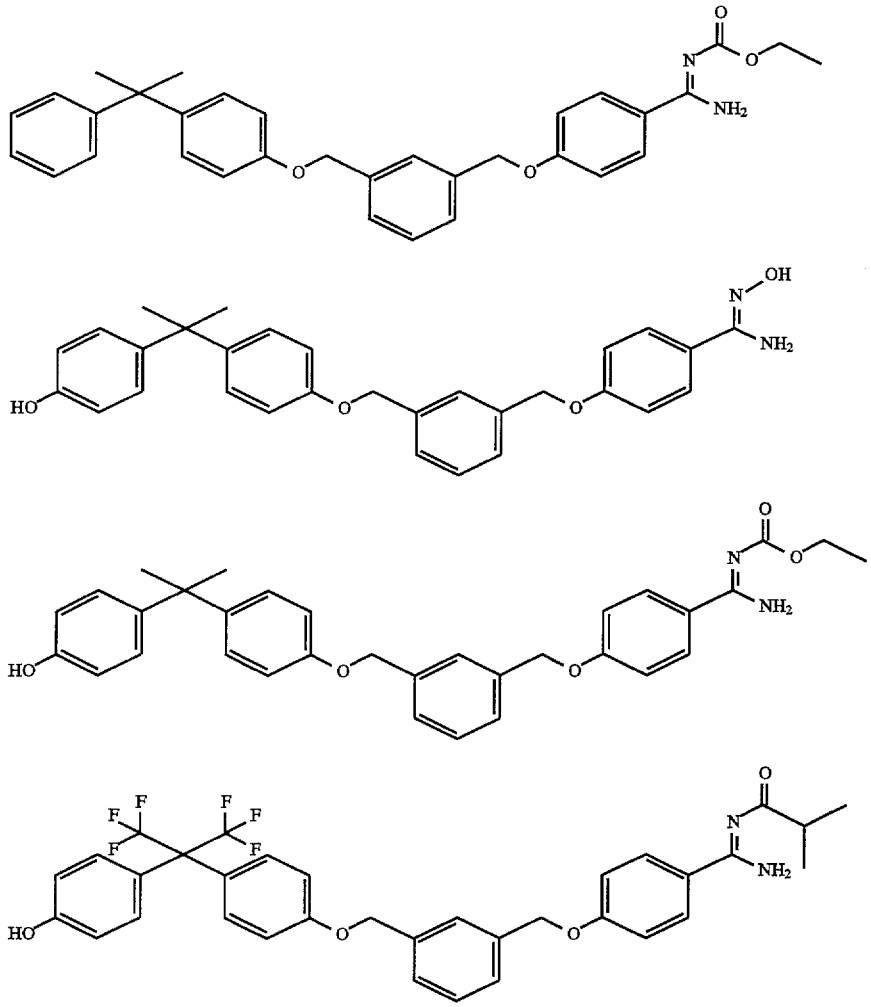

We claim:

1. A compound of the formula

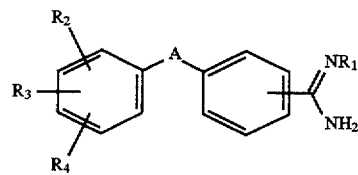

wherein

A denotes the group

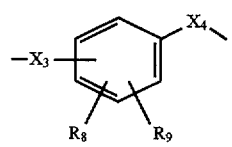

$X_1$ denotes O, NH or $NCH_3$ $X_2$ denotes O, NH, $NCH_3$ or

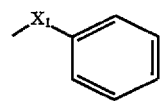

$X_3$ denotes $-X-C_nH_{2n}-$;
$X_4$ denotes $-C_nH_{2n}-X-$;
n denotes 1 or 2;
X denotes O, NH or $NCH_3$;
$R_1$ denotes OH, CN, $COR_{12}$, $COOR_{12}$ or CHO;
$R_2$ denotes H (provided that A is a group of Formula III or $X_2$ is a group of Formula IV), Br, Cl, F, $CF_3$, OH, $C_1$–$C_6$-alkyl, $C_5$–$C_7$-cycloalkyl, $C_1$–$C_6$-alkoxy (provided that A is the group II, $X_1$ is as hereinbefore defined and $X_2$ denotes NH, $NCH_3$ or the group IV, or provided that A denotes the group III, $X_3$ is as hereinbefore defined and, in $X_4$, X denotes NH or $NCH_3$), aryl, O-acryl, $CH_2$-aryl, $CR_5R_6$-aryl, or $C(CH_3)_2$-$R_7$;
$R_3$ denotes H, $C_1$–$C_6$-alkyl, OH, Cl, F, and also $C_1$–$C_6$ alkoxy when $R_2$ denotes aryl, O-aryl, $CH_2$-aryl, $CR_5R_6$-aryl or $C(CH_3)_2$-$R_7$ or when $X_2$ denotes the group IV;
$R_2$ and $R_3$, in the alternative, may also together denote a fused aromatic or heteroaromatic ring;

$R_4$ denotes H or $C_1$–$C_6$-alkyl;

$R_5$ denotes $C_1$–$C_4$-alkyl, $CF_3$, $CH_2OH$, COOH or COO($C_1$–$C_4$-alkyl);

$R_6$ denotes H, $C_1$–$C_4$-alkyl, or $CF_3$;

$R_5$ and $R_6$, in the alternative, may also together form a $C_4$–$C_6$-alkylene group;

$R_7$ denotes $CH_2OH$, COOH, COO($C_1$–$C_4$-alkyl), $CONR_{10}R_{11}$ or $CH_2NR_{10}R_{11}$;

$R_8$ and $R_9$ each independently denote H, Br, Cl, F, OH, $C_1$–$C_6$-alkyl or $C_1$–$C_6$-alkoxy;

$R_{10}$ denotes H, $C_1$–$C_6$-alkyl, phenyl, phenyl-($C_1$–$C_6$-alkyl), $COR_{12}$, $COOR_{12}$, CHO, $CONH_2$, $CONHR_{12}$, $SO_2$-($C_1$–$C_6$-alkyl), $SO_2$-phenyl, wherein each of the phenyl groups may be mono- or polysubstituted by groups selected from Cl, F, $CF_3$, $C_1$–$C_4$-alkyl, OH and $C_1$–$C_4$-alkoxy;

$R_{11}$ denotes H or $C_1$–$C_6$-alkyl;

$R_{10}$ and $R_{11}$, in the alternative, may also together denote a $C_4$–$C_6$-alkylene group; and, $R_{12}$ denotes $C_1$–$C_6$-alkyl, $C_5$–$C_7$-cycloalkyl, aryl, heteroaryl, aralkyl or heteroaryl-($C_1$–$C_6$-alkyl), wherein the aryl or heteroaryl group may be mono or polysubstituted by Cl, F, $CF_3$, $C_1$–$C_4$-alkyl, OH or $C_1$–$C_4$-alkoxy;

wherein each of the above-mentioned aryl groups denotes phenyl and each of the above-mentioned heteroaryl groups denotes pyridyl, pyrimidyl, pyridazinyl, pyrazinyl, thienyl or furyl, and wherein each such aryl or heteroaryl group is, unless otherwise specified, either unsubstituted or mono- or poly-substituted with a group selected from Cl, F, Br, OH, $C_1$–$C_6$-alkyl, $C_1$–$C_6$-alkoxy and $CF_3$;

or a tautomer or pharmaceutically acceptable salt thereof; with the proviso that if A denotes a group —$X_1$—$C_mH_{2m}$—$X_2$—
wherein m represents an integer 2, 3, or 4;

$X_1$ denotes O, NH;

$X_2$ denotes O, NH or

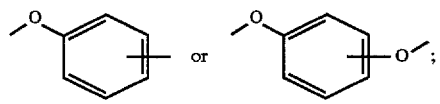

$R_2$ denotes hydrogen, Br, Cl, $CF_3$, $C_1$–$C_6$-alkyl, phenyl;

$R_3$ denotes hydrogen, $C_1$–$C_6$-alkyl, hydroxy, Cl, F, $C_1$–$C_6$-alkoxy; and, $R_4$ denotes hydrogen, $C_1$–$C_6$-alkyl; then, $R_1$ must not denote hydroxy.

2. A compound of the formula I, in accordance with claim 1, wherein, $X_1$ denotes O;

$X_2$ denotes O or a group IV (wherein $X_1$ equals O);

$R_2$ denotes Cl, F, $CF_3$, OH, $C_1$–$C_6$-alkyl, aryl, O-aryl, $CH_2$-aryl or $CR_5R_6$-aryl, and, if $X_2$ is the group IV, $R_2$ may also represent $C_1$–$C_6$-alkoxy;

$R_3$ denotes H, $C_1$–$C_6$-alkyl or OH, and, if $R_2$ is $CR_5R_6$-aryl, $R_3$ may also denote $C_1$–$C_6$-alkoxy;

$R_4$ denotes H;

$R_5$ denotes $C_1$–$C_3$-alkyl, $CF_3$ or $CH_2OH$;

$R_6$ denotes H, $C_1$–$C_3$-alkyl or $CF_3$, $R_5$ and $R_6$ together may also denote $C_4$–$C_5$-alkylene; and, $R_8$ and $R_9$ each independently denote H, F or OH.

3. A compound of the formula I, in accordance with claim 1, wherein $X_1$ denotes O;

$X_2$ denotes the group IV (wherein $X_1$ equals O);

X denotes O;

$R_1$ denotes $COOR_{12}$;

$R_2$ denotes $C_1$–$C_6$-alkyl, aryl, O-aryl, $CH_2$-aryl or $CR_5R_6$-aryl;

$R_3$ denotes H, OH or $C_1$–$C_6$-alkyl and, if $R_2$ is $CR_5R_6$-aryl, $R_3$ may also denote $C_1$–$C_6$ alkoxy;

$R_4$ denotes H;

$R_5$ and $R_6$ each independently denote $C_1$–$C_3$-alkyl or $CF_3$;

$R_8$ and $R_9$ each denote H; and, $R_{12}$ denotes $C_1$–$C_6$-alkyl, aralkyl or $C_7$–$C_5$-cycloalkyl.

4. (Methoxycarbonyl-imino-{4'-[2-(2-propylphenoxy)-ethoxy]-biphenyl-4-yl}-methyl)-amine or a pharmaceutically acceptable salt thereof.

5. (Benzyloxycarbonyl-imino-{4'-[2-(2-propylphenoxy)-ethoxy]-biphenyl-4-yl}-methyl)-amine or a pharmaceutically acceptable salt thereof.

6. [Hydroxy-imino-(4-{3-[4-(1-methyl-1-phenylethyl)-phenoxymethyl]-benzoyloxy}phenyl)-methyl]-amine or a pharmaceutically acceptable salt thereof.

7. [Ethoxycarbonyl-imino-(4-{3-[4-(1-methyl-1-phenylethyl)-phenoxymethyl]-benzoyloxy}phenyl)-methyl]-amine or a pharmaceutically acceptable salt thereof.

8. [3'-Pyridylcarbonyl-imino-(4-{3-[4-(1-methyl-1-phenylethyl)-phenoxymethyl]-benzyloxy}phenyl)-methyl]-amine or a pharmaceutically acceptable salt thereof.

9. A pharmaceutical composition comprising a compound of the formula I, in accordance with claim 1, and a pharmacologically acceptable diluent, excipient or carrier.

10. A method for treating an inflammatory disease which comprises administering a compound of the formula

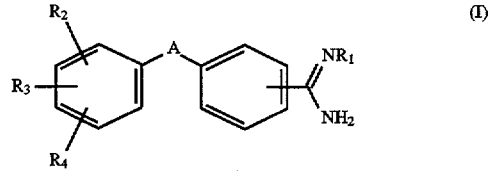
(I)

wherein

A denotes the group

(II)

(m equals 2 to 6)

or

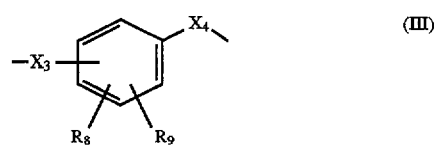
(III)

$X_1$ denotes O, NH or $NCH_3$ $X_2$ denotes O, NH, $NCH_3$ or

(IV)

$X_3$ denotes —X—$C_nH_{2n}$—;

$X_4$ denotes —$C_nH_{2n}$—X—;

n denotes 1 or 2;

X denotes O, NH or $NCH_3$;

$R_1$ denotes OH, CN, $COR_{12}$, $COOR_{12}$ or CHO;

$R_2$ denotes H (provided that A is a group of Formula III or $X_2$ is a group of Formula IV), Br, Cl, F, $CF_3$, OH, $C_1$–$C_6$-alkyl, $C_5$–$C_7$-cycloalkyl, $C_1$–$C_6$-alkoxy (provided that A is the group II, $X_1$ is as hereinbefore defined and $X_2$ denotes NH, $NCH_3$ or the group IV, or provided that A denotes the group III, $X_3$ is as hereinbefore defined and, in $X_4$, X denotes NH or $NCH_3$), aryl, O-aryl, $CH_2$-aryl, $CR_5R_6$-aryl, or $C(CH_3)\%_2$-$R_7$;

$R_3$ denotes H, $C_1$–$C_6$-alkyl, OH, Cl, F, and also $C_1$–$C_6$ alkoxy when $R_2$ denotes aryl, O-aryl, $CH_2$-aryl, $CR_5R_6$-aryl or $C(CH_3)_2$-$R_7$ or when $X_2$ denotes the group IV;

$R_2$ and $R_3$, in the alternative, may also together denote a fused aromatic or heteroaromatic ring;

$R_4$ denotes H or $C_1$–$C_6$-alkyl;

$R_5$ denotes $C_1$–$C_4$-alkyl, $CF_3$, $CH_2OH$, COOH or COO($C_1$–$C_4$-alkyl);

$R_6$ denotes H, $C_1$–$C_4$-alkyl, or $CF_3$;

$R_5$ and $R_6$, in the alternative, may also together form a $C_4$–$C_6$-alkylene group;

$R_7$ denotes $CH_2OH$, COOH, COO($C_1$–$C_4$-alkyl), $CONR_{10}R_{11}$ or $CH_2NR_{10}R_{11}$;

$R_8$ and $R_9$ each independently denote H, Br, Cl, F, OH, $C_1$–$C_6$-alkyl or $C_1$–$C_6$-alkoxy;

$R_{10}$ denotes H, $C_1$–$C_6$-alkyl, phenyl, phenyl-($C_1$–$C_6$-alkyl), $COR_{12}$, $COOR_{12}$, CHO, $CONH_2$, $CONHR_{12}$, $SO_2$-($C_1$–$C_6$-alkyl), $SO_2$-phenyl, wherein each of the phenyl groups may be mono- or polysubstituted by groups selected from Cl, F, $CF_3$, $C_1$–$C_4$-alkyl, OH and $C_1$–$C_4$-alkoxy;

$R_{11}$ denotes H or $C_1$–$C_6$-alkyl;

$R_{10}$ and $R_{11}$, in the alternative, may also together denote a $C_4$–$C_6$-alkylene group; and, $R_{12}$ denotes $C_1$–$C_6$-alkyl, $C_5$–$C_7$-cycloalkyl, aryl, heteroaryl, aralkyl or heteroaryl-($C_1$–$C_6$-alkyl), wherein the aryl or heteroaryl group may be mono or polysubstituted by Cl, F, $CF_3$, $C_1$–$C_4$-alkyl, OH or $C_1$–$C_4$-alkoxy;

wherein each of the above-mentioned aryl groups denotes phenyl and each of the above-mentioned heteroaryl groups denotes pyridyl, pyrimidyl, pyridazinyl pyrazinyl, thienyl or furyl, and wherein each such aryl or heteroaryl group is, unless otherwise specified, either unsubstituted or mono- or poly-substituted with a group selected from Cl, F, Br, OH, $C_1$–$C_6$-alkyl, $C_1$–$C_6$-alkoxy and $CF_3$;

or a tautomer or pharmaceutically acceptable salt thereof.

11. A method for treating an allergic process which comprises administering a therapeutic amount of a compound of the formula

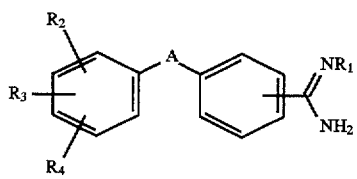

(I)

wherein

A denotes the group

—$X_1$—$C_mH_{2m}$—$X_2$— (II)

(m equals 2 to 6)

or

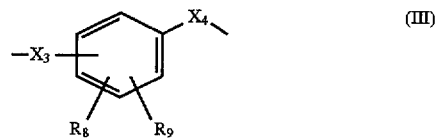

(III)

$X_1$ denotes O, NH or $NCH_3$ $X_2$ denotes O, NH, $NCH_3$ or

(IV)

$X_3$ denotes —X—$C_nH_{2n}$—;

$X_4$ denotes —$C_nH_{2n}$—X—;

n denotes 1 or 2;

X denotes O, NH or $NCH_3$;

$R_1$ denotes OH, CN, $COR_{12}$, $COOR_{12}$ or CHO;

$R_2$ denotes H (provided that A is a group of Formula III or $X_2$ is a group of Formula IV), Br, Cl, F, $CF_3$, OH, $C_1$–$C_6$alkyl, $C_5$–$C_7$cycloalkyl, $C_1$–$C_6$: alkoxy (provided that A is the group II, $X_1$ is as hereinbefore defined and $X_2$ denotes NH, $NCH_3$ or the group IV, or provided that A denotes the group III, $X_3$ is as hereinbefore defined and, in $X_4$, X denotes NH or $NCH_3$), aryl, O-aryl, $CH_2$-aryl, $CR_5R_6$-aryl, or $C(CH_3)_2$-$R_7$;

$R_3$ denotes H, $C_1$–$C_6$-alkyl, OH, Cl, F, and also $C_1$–$C_6$ alkoxy when $R_2$ denotes aryl, O-aryl, $CH_2$-aryl, $CR_5R_6$-aryl or $C(CH_3)_2$-$R_7$ or when $X_2$ denotes the group IV;

$R_2$ and $R_3$, in the alternative, may also together denote a fused aromatic or heteroaromatic ring;

$R_4$ denotes H or $C_1$–$C_6$-alkyl;

$R_5$ denotes $C_1$–$C_4$-alkyl, $CF_3$, $CH_2OH$, COOH or COO($C_1$–$C_4$-alkyl);

$R_6$ denotes H, $C_1$–$C_4$-alkyl, or $CF_3$;

$R_5$ and $R_6$, in the alternative, may also together form a $C_4$–$C_6$-alkylene group;

$R_7$ denotes $CH_2OH$, COOH, COO($C_1$–$C_4$-alkyl), $CONR_{10}R_{11}$ or $CH_2NR_{10}R_{11}$;

$R_8$ and $R_9$ each independently denote H, Br, Cl, F, OH, $C_1$–$C_6$-alkyl or $C_1$–$C_6$-alkoxy;

$R_{10}$ denotes H, $C_1$–$C_6$-alkyl, phenyl, phenyl-($C_1$–$C_6$-alkyl), $COR_{12}$, $COOR_{12}$, CHO, $CONH_2$, $CONHR_{12}$, $SO_2$-($C_1$–$C_6$-alkyl), $SO_2$-phenyl, wherein each of the phenyl groups may be mono- or polysubstituted by groups selected from Cl, F, $CF_3$, $C_1$–$C_4$-alkyl, OH and $C_1$–$C_4$-alkoxy;

$R_{11}$ denotes H or $C_1$–$C_6$-alkyl;

$R_{10}$ and $R_{11}$, in the alternative, may also together denote a $C_4$–$C_6$-alkylene group; and, $R_{12}$ denotes $C_1$–$C_6$-alkyl, $C_5$–$C_7$-cycloalkyl, aryl, heteroaryl, aralkyl or heteroaryl-($C_1$–$C_6$-alkyl), wherein the aryl or heteroaryl group may be mono or polysubstituted by Cl, F, $CF_3$, $C_1$–$C_4$-alkyl, OH or $C_1$–$C_4$-alkoxy;

wherein each of the above-mentioned aryl groups denotes phenyl and each of the above-mentioned heteroaryl groups denotes pyridyl, pyrimidyl, pyridazinyl, pyrazinyl, thienyl or furyl, and wherein each such aryl or heteroaryl group is, unless otherwise specified, either unsubstituted or mono- or poly-substituted with a group selected from Cl, F, Br, OH, $C_1$–$C_6$-alkyl, $C_1$–$C_6$-alkoxy and $CF_3$;

or a tautomer or pharmaceutically acceptable salt thereof.

12. A method for treating a condition selected from the group consisting of arthritis, asthma, chronic obstructive lung diseases, psoriasis, ulcerative colitis, Alzheimer's disease, shock, atherosclerosis, and multiple sclerosis, which comprises administering a compound of the formula

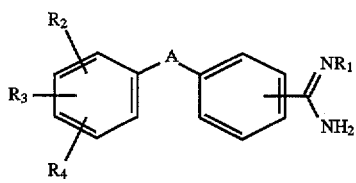

(I)

wherein

A denotes the group

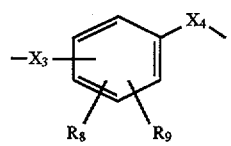

(III)

$X_1$ denotes O, NH or $NCH_3$ $X_2$ denotes O, NH, $NCH_3$ or

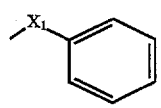

(IV)

$X_3$ denotes —X—$C_nH_{2n}$—;
$X_4$ denotes —$C_nH_{2n}$—X—;
n denotes 1 or 2;
X denotes O, NH or $NCH_3$:
$R_1$ denotes OH, CN, $COR_{12}$, $COOR_{12}$ or CHO;
$R_2$ denotes H (provided that A is a group of Formula III or $X_2$ is a group of Formula IV), Br, Cl, F, $CF_3$, OH, $C_1$–$C_6$-alkyl, $C_5$–$C_7$-cycloalkyl, $C_1$–$C_6$-alkoxy (provided that A is the group II, $X_1$ is as hereinbefore defined and $X_2$ denotes NH, $NCH_3$ or the group IV, or provided that A denotes the group III, $X_3$ is as hereinbefore defined and, in $X_4$, X denotes NH or $NCH_3$), aryl, O-aryl, $CH_2$-aryl, $CR_5R_6$-aryl, or $C(CH_3)_2$-$R_7$;

$R_3$ denotes H, $C_1$–$C_6$-alkyl, OH, Cl, F, and also $C_1$–$C_6$ alkoxy when $R_2$ denotes aryl, O-aryl, $CH_2$-aryl, $CR_5R_6$-aryl or $C(CH_3)_2$-$R_7$ or when $X_2$ denotes the group IV;

$R_2$ and $R_3$, in the alternative, may also together denote a fused aromatic or heteroaromatic ring;

$R_4$ denotes H or $C_1$–$C_6$-alkyl;

$R_5$ denotes $C_1$–$C_4$-alkyl, $CF_3$, $CH_2OH$, COOH or COO($C_1$–$C_4$-alkyl);

$R_6$ denotes H, $C_1$–$C_4$-alkyl, or $CF_3$;

$R_5$ and $R_6$, in the alternative, may also together form a $C_4$–$C_6$-alkylene group;

$R_7$ denotes $CH_2OH$, COOH, COO($C_1$–$C_4$-alkyl), $CONR_{10}R_{11}$ or $CH_2NR_{10}R_{11}$;

$R_8$ and $R_9$ each independently denote H, Br, Cl, F, OH, $C_1$–$C_6$-alkyl or $C_1$–$C_6$-alkoxy;

$R_{10}$ denotes H, $C_1$–$C_6$-alkyl, phenyl, phenyl-($C_1$–$C_6$-alkyl), $COR_{12}$, $COOR_{12}$, CHO, $CONH_2$, $CONHR_{12}$, $SO_2$-($C_1$–$C_6$-alkyl), $SO_2$-phenyl, wherein each of the phenyl groups may be mono- or polysubstituted by groups selected from Cl, F, $CF_3$, $C_1$–$C_4$-alkyl, OH and $C_1$–$C_4$-alkoxy;

$R_{11}$ denotes H or $C_1$–$C_6$-alkyl;

$R_{10}$ and $R_{11}$, in the alternative, may also together denote a $C_4$–$C_6$-alkylene group; and, $R_{12}$ denotes $C_1$–$C_6$-alkyl, $C_5$–$C_7$-cycloalkyl, aryl, heteroaryl, aralkyl or heteroaryl-($C_1$–$C_6$-alkyl), wherein the aryl or heteroaryl group may be mono or polysubstituted by Cl, F, $CF_3$, $C_1$–$C_4$-alkyl, OH or $C_1$–$C_4$-alkoxy;

wherein each of the above-mentioned awl groups denotes phenyl and each of the above-mentioned heteroaryl groups denotes pyridyl, pyrimidyl, pyridazinyl, pyrazinyl, thienyl or furyl, and wherein each such awl or heteroaryl group is, unless otherwise specified, either unsubstituted or mono- or poly-substituted with a group selected from Cl, F, Br, OH, $C_1$–$C_6$-alkyl, $C_1$–$C_6$-alkoxy and $CF_3$;

or a tautomer or pharmaceutically acceptable salt thereof.

13. A method for treating of gastropathy induced by a non-steroidal anti-inflammatory agent which comprises administering a therapeutic amount of a compound of the formula

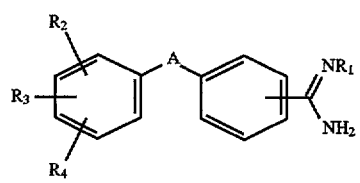

(I)

wherein

A denotes the group

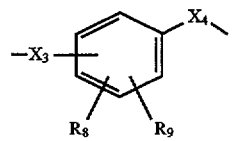

(III)

$X_1$ denotes O, NH or $NCH_3$
$X_2$ denotes O, NH, $NCH_3$ or

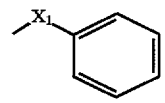

(IV)

$X_3$ denotes —X—$C_nH_{2n}$—;
$X_4$ denotes —$C_nH_{2n}$—X—;
n denotes 1 or 2;
X denotes O, NH or $NCH_3$:
$R_1$ denotes OH, CN, $COR_{12}$, $COOR_{12}$ or CHO;
$R_2$ denotes H (provided that A is a group of Formula III or $X_2$ is a group of Formula IV), Br, Cl, F, $CF_3$, OH, $C_1$–$C_6$-alkyl, $C_5$–$C_7$-cycloalkyl, $C_1$–$C_6$-alkoxy (provided that A is the group II, $X_1$ is as hereinbefore defined and $X_2$ denotes NH, $NCH_3$ or the group IV, or provided that A denotes the group III, $X_3$ is as hereinbefore defined and, in $X_4$, X denotes NH or $NCH_3$), aryl, O-aryl, $CH_2$-aryl, $CR_5R_6$-aryl, or $C(CH_3)_2$-$R_7$;

$R_3$ denotes H, $C_1$–$C_6$-alkyl, OH, Cl, F, and also $C_1$–$C_6$ alkoxy when $R_2$ denotes aryl, O-aryl, $CH_2$-aryl, $CR_5R_6$-aryl or $C(CH_3)_2$-$R_7$ or when $X_2$ denotes the group IV;

$R_2$ and $R_3$, in the alternative, may also together denote a fused aromatic or heteroaromatic ring;

$R_4$ denotes H or $C_1$–$C_6$-alkyl;

$R_5$ denotes $C_1$–$C_4$-alkyl, $CF_3$, $CH_2OH$, COOH or COO($C_1$–$C_4$-alkyl);

$R_6$ denotes H, $C_1$–$C_4$-alkyl, or $CF_3$;

$R_5$ and $R_6$, in the alternative, may also together form a $C_4$–$C_6$-alkylene group;

$R_7$ denotes $CH_2OH$, COOH, COO($C_1$–$C_4$-alkyl), $CONR_{10}R_{11}$ or $CH_2NR_{10}R_{11}$;

$R_8$ and $R_9$ each independently denote H, Br, Cl, F, OH, $C_1$–$C_6$-alkyl or $C_1$–$C_6$-alkoxy;

$R_{10}$ denotes H, $C_1$–$C_6$-alkyl, phenyl, phenyl-($C_1$–$C_6$-alkyl), $COR_{12}$, $COOR_{12}$, CHO, $CONH_2$, $CONHR_{12}$, $SO_2$-($C_1$–$C_6$-alkyl), $SO_2$-phenyl, wherein each of the phenyl groups may be mono- or polysubstituted by groups selected from Cl, F, $CF_3$, $C_1$–$C_4$-alkyl, OH and $C_1$–$C_4$-alkoxy;

$R_{11}$ denotes H or $C_1$–$C_6$-alkyl;

$R_{10}$ and $R_{11}$, in the alternative, may also together denote a $C_4$–$C_6$-alkylene group; and, $R_{12}$ denotes $C_1$–$C_6$-alkyl, $C_5$–$C_7$-cycloalkyl, aryl, heteroaryl, aralkyl or heteroaryl-($C_1$–$C_6$-alkyl), wherein the aryl or heteroaryl group may be mono or polysubstituted by Cl, F, $CF_3$, $C_1$–$C_4$-alkyl, OH or $C_1$–$C_4$-alkoxy;

wherein each of the above-mentioned aryl groups denotes phenyl and each of the above-mentioned heteroaryl groups denotes pyridyl, pyrimidyl, pyridazinyl, pyrazinyl, thienyl or furyl, and wherein each such aryl or heteroaryl group is, unless otherwise specified, either unsubstituted or mono- or poly-substituted with a group selected from Cl, F, Br, OH, $C_1$–$C_6$-alkyl, $C_1$–$C_6$-alkoxy and $CF_3$;

or a tautomer or pharmaceutically acceptable salt thereof.

14. A method for treating metastasis and chronic myelocytic leukaemia which comprises administering a therapeutic amount of a compound of the formula

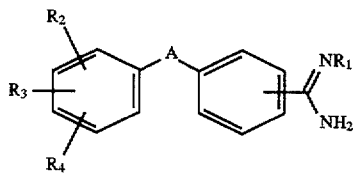

(I)

wherein

A denotes the group

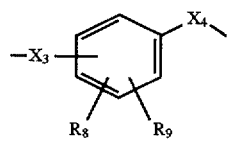

(III)

$X_1$ denotes O, NH or $NCH_3$ $X_2$ denotes O, NH, $NCH_3$ or

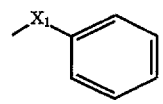

(IV)

$X_3$ denotes —X—$C_nH_{2n}$—;

$X_4$ denotes —$C_nH_{2n}$—X—;

n denotes 1 or 2;

X denotes O, NH or $NCH_3$;

$R_1$ denotes OH, CN, $COR_{12}$, $COOR_{12}$ or CHO;

$R_2$ denotes H (provided that A is a group of Formula III or $X_2$ is a group of Formula IV), Br, Cl, F, $CF_3$, OH, $C_1$–$C_6$-alkyl, $C_5$–$C_7$-cycloalkyl, $C_1$–$C_6$-alkoxy (provided that A is the group II, $X_1$ is as hereinbefore defined and $X_2$ denotes NH, $NCH_3$ or the group IV, or provided that A denotes the group III, $X_3$ is as hereinbefore defined and, in $X_4$, X denotes NH or $NCH_3$), aryl, O-aryl, $CH_2$-aryl, $CR_5R_6$-aryl, or $C(CH_3)_2$-$R_7$;

$R_3$ denotes H, $C_1$–$C_6$-alkyl, OH, Cl, F, and also $C_1$–$C_6$ alkoxy when $R_2$ denotes aryl, O-aryl, $CH_2$-aryl, $CR_5R_6$-aryl or $C(CH_3)_2$-$R_7$ or when $X_2$ denotes the group IV;

$R_2$ and $R_3$, in the alternative, may also together denote a fused aromatic or heteroaromatic ring;

$R_4$ denotes H or $C_1$–$C_6$-alkyl;

$R_5$ denotes $C_1$–$C_4$-alkyl, $CF_3$, $CH_2OH$, COOH or COO($C_1$–$C_4$-alkyl);

$R_6$ denotes H, $C_1$–$C_4$-alkyl, or $CF_3$;

$R_5$ and $R_6$, in the alternative, may also together form a $C_4$–$C_6$-alkylene group;

$R_7$ denotes $CH_2OH$, COOH, COO($C_1$–$C_4$-alkyl), $CONR_{10}R_{11}$ or $CH_2NR_{10}R_{11}$;

$R_8$ and $R_9$ each independently denote H, Br, Cl, F, OH, $C_1$–$C_6$-alkyl or $C_1$–$C_6$-alkoxy;

$R_{10}$ denotes H, $C_1$–$C_6$-alkyl, phenyl, phenyl-($C_1$–$C_6$-alkyl), $COR_{12}$, $COOR_{12}$, CHO, $CONH_2$, $CONHR_{12}$, $SO_2$-($C_1$–$C_6$-alkyl), $SO_2$-phenyl, wherein each of the phenyl groups may be mono- or polysubstituted by groups selected from Cl, F, $CF_3$, $C_1$–$C_4$-alkyl, OH and $C_1$–$C_4$-alkoxy;

$R_{11}$ denotes H or $C_1$–$C_6$-alkyl;

$R_{10}$ and $R_{11}$, in the alternative, may also together denote a $C_4$–$C_6$-alkylene group; and, $R_{12}$ denotes $C_1$–$C_6$-alkyl, $C_5$–$C_7$-cycloalkyl, aryl, heteroaryl, aralkyl or heteroaryl-($C_1$–$C_6$-alkyl), wherein the aryl or heteroaryl group may be mono or polysubstituted by Cl, F, $CF_3$, $C_1$–$C_4$-alkyl, OH or $C_1$–$C_4$-alkoxy;

wherein each of the above-mentioned aryl groups denotes phenyl and each of the above-mentioned heteroaryl groups denotes pyridyl, pyrimidyl, pyridazinyl, pyrazinyl, thienyl or furyl, and wherein each such aryl or heteroaryl group is, unless otherwise specified, either unsubstituted or mono- or poly-substituted with a group selected from Cl, F, Br, OH, $C_1$–$C_6$C-alkyl, $C_1$–$C_6$-alkoxy and $CF_3$;

or a tautomer or pharmaceutically acceptable salt thereof.

* * * * *